United States Patent [19]

Chatanier et al.

[11] Patent Number: 4,546,310
[45] Date of Patent: Oct. 8, 1985

[54] ELECTRICAL CONTINUIMETER

[75] Inventors: Michel J. Chatanier, Saint Maur; Michel J. Portat, Villebon-sur-Yvette; Alain E. Bruère, Chevilly-Larue, all of France

[73] Assignee: Office National d'Etudes et de Recherches Aerospatiales (O.N.E.R.A.), Chatillon, France

[21] Appl. No.: 539,815

[22] Filed: Oct. 7, 1983

Related U.S. Application Data

[63] Continuation-in-part of Ser. No. 302,618, Sep. 15, 1981, Pat. No. 4,446,424.

[30] Foreign Application Priority Data

Oct. 17, 1980 [FR] France ............................... 80 22329

[51] Int. Cl.⁴ ..................... G01R 27/02; G01R 27/26
[52] U.S. Cl. ...................................... 324/52; 324/62; 324/65 P; 324/61 P
[58] Field of Search ............... 324/61 R, 61 P, 62, 324/51, 64, 52, 65 P

[56] References Cited

U.S. PATENT DOCUMENTS

| | | | |
|---|---|---|---|
| 4,075,557 | 2/1978 | Jurca | 324/62 |
| 4,218,650 | 8/1980 | Matzen | 324/62 |
| 4,335,350 | 6/1982 | Chen | 324/62 |

FOREIGN PATENT DOCUMENTS 1333449  9/1962  France.

OTHER PUBLICATIONS

Batt: "Surface Resistivity and Power Measurement"—Colloquium on the Measurement of Power at Higher Microwave Freqs.—London, UK., Jan. 1979.
Phillips: "Versatile Four Probe AC Conductivity Measurement System" Rev. Sci. Instruments—Feb. 1979, pp. 263-265.

Primary Examiner—Stanley T. Krawczewicz
Assistant Examiner—Jose M. Solis
Attorney, Agent, or Firm—Lowe, King, Price & Becker

[57] ABSTRACT

Electrical continuimeter device for checking the electrical continuity of a conducting layer covering a structure having conducting and non-conducting parts, said conducting layer being covered by an insulator layer. The device comprises a pick-up with an inner and an outer coaxial electrodes to be put on the insulator layer. A supply alternating voltage is applied between the inner electrode and the ground terminal of the structure developing a first voltage across a load resistor and a second voltage between the outer electrode and the ground terminal is measured. Components of the second voltage respectively cophasal and in phase quadrature with the first voltage are generated and these components are divided by the first voltage, thus providing the resistive and reactive components of the ground impedance.

4 Claims, 7 Drawing Figures

ELECTRICAL CONTINUIMETER

The present application is a continuation-in-part of our patent application Ser. No. 302,618, filed Sept. 15, 1981, now U.S. Pat. No. 4,446,424, issued May 1, 1984.

BACKGROUND OF THE INVENTION

1. Field of the Invention

The present invention concerns an antistatic surface coating checking device intended for ensuring that a structure made up of a metal frame including both metal panels and insulating panels coated with a layer of conducting material, the surface of these panels being entirely finished with an insulating paint, is capable of withstanding the action of the electrostatic phenomena to which it is subjected with no adverse effect. To be more precise, this device makes it possible to verity that the panels are indeed electrically grounded to the metal frame with a view to checking out the effectiveness of the antistatic protection provided by the conducting layer covering the structure insulating elements.

The antistatic protective measures, particularly those employed in the aerospace industry, can be broken down into two categories:

those applied to structural elements not requiring radioelectric transparency properties (example: access doors, wing sections, tip ends, etc.);

those applied to the dielectric walls protecting navigation, communication or detection equipment and consequently calling for radioelectric transparency properties (example: radome, aerial fairings, missile caps, etc.).

In the first case, the antistatic deposits applied can have very low surface resistance values. In the second case, the deposits made must provide high and perfectly controlled surface resistances in order to afford a compromise between the continual flow of static charges and the necessary radio-transparency properties. This compromise gives rise, in the majority of applications, to surface resistances lying between $10_5$ and $10^8$ ohms per square.

In virtually all aerospace applications (airplanes, helicopters, missiles), the antistatic treatments are themselves followed by the application of a finishing paint (for the purposes of aesthetics as regards commercial aircraft, optical detection for the experimental missiles, particle impact resistance, corrosion immunity, thermal balance, etc.). This finishing paint is an insulator and rules out, on the face of it, any process for measuring or checking the subjacent electrostatic protection using electrodes in electrical contact (megohmmeter with plane or circular electrodes).

2. Description of the Prior Art

French Pat. No. 1 333 449 filed Sept. 12, 1962 discloses a surface resistivimeter having central and annular coaxial electrodes made of conducting rubber. This resistivimeter permits the measurement of the resistance of bare metallic surfaces; it cannot measure the resistances of surfaces coated with an insulating layer, nor it can test electrical continuity of a structure having a ground terminal.

SUMMARY OF THE INVENTION

The object of the invention is to provide a continuimeter adapted for checking electrical continuity between the ground terminal of a structure and a metal element of this structure or a metal coating on a structure insulating element, said metal element or said metal coating being covered by an insulating layer.

Another object of the invention is to provide a continuimeter device able of measuring the resistive component and the reactive component of the ground impedance.

Another object of the invention is to provide a continuimeter device able of measuring the ground impedance of a structure and to decide when this impedance is low that it is because the ground resistance is small and not because the ground capacitance is high.

The electrical continuimeter device of this invention comprises a pick-up with an inner and an outer coaxial electrodes to be put on the insulator layer. A supply alternating voltage is applied between the inner electrode and the ground terminal of the structure, developing a first voltage across a load resistor, and a second voltage between the outer electrode and the ground terminal is measured. The components of the second voltage respectively cophasal and in phase quadrature with the first voltage are generated and these components are divided by the first voltage thus providing the resistive and reactive components of the ground impedance and these components are compared with predetermined limits.

BRIEF DESCRIPTION OF THE DRAWINGS

The invention will now be described in detail with reference being made to the drawings in appendix hereto in which.

DESCRIPTION OF THE PREFERRED EMBODIMENTS

Figure 1A:
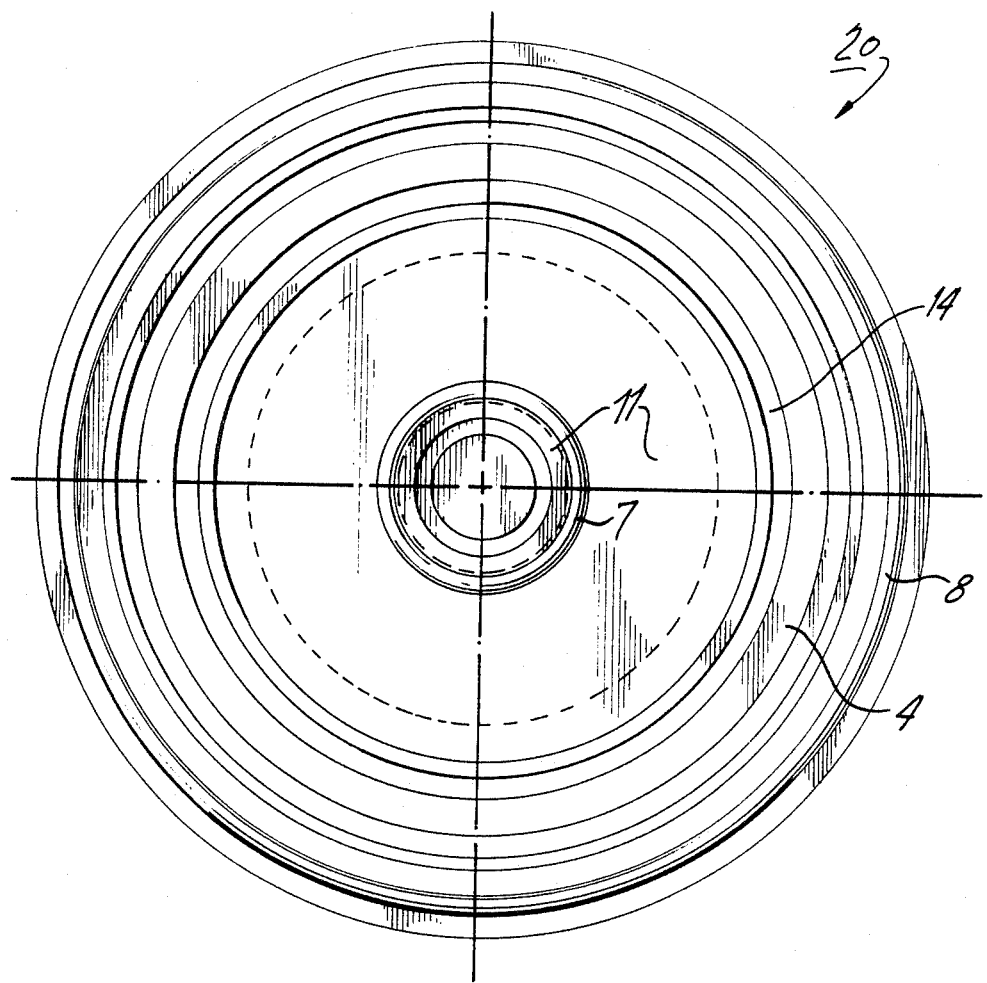
FIGS. 1A and 1B depict the pick-up of the continuimeter of the invention.

The following symbols are used hereinafter:

$R_T$ is the resistance between the outer electrode and the ground;

$C_1$, $C_4$ are the capacitances between the faces of the inner and outer electrodes resting on the insulating layer and the resistive layer situated beneath this insulating layer;

$C_T$ is the capacitance of the device with respect to the ground;

$\gamma$ is the capacitance between the inner and outer electrodes across the insulating layer;

$i$ is the current flowing in the resistance $R_T$ and the capacitance $\gamma$;

R is the value of a load resistor across which the voltage $V_{ef}$ is measured;

The electrical supply is fed between the central electrode and the ground. The device verifies that the impedance ($R_T$, $C_T$) is less than a certain given value and that this impedance is low, not because the capacitance $C_T$ is high but because the resistance $R_T$ is small. The device measures two voltages $V_{ef}$ across the load resistor terminals and $V_{de}$ across the terminals of the impedance to be measured and forms the voltage components $V^p_{de}$ and $V^q_{de}$ respectively in phase and in quadrature with the voltage $V_{ef}$. It then performs the divisions:

$$V^p_{de}/|V_{ef}| = \frac{R_T}{R} \times \frac{1}{R_T^2 C_T^2 \omega^2 + 1} \qquad (1)$$

$$V^q_{de}/|V_{ef}| = \frac{R_T}{R} \times \frac{R_T C_T \omega}{R_T^2 C_T^2 \omega^2 + 1} \qquad (2)$$

The device checks that these resistive and reactive impedance components are less than or equal to predetermined limits:

$$R_T \times \frac{1}{R_T^2 C_T^2 \omega^2 + 1} \leq a \qquad (3)$$

$$R_T \times \frac{R_T C_T \omega}{R_T^2 C_T^2 \omega^2 + 1} \leq B \qquad (4)$$

Confirmation of inequality (4) provides firm proof that the confirmation of inequality (3) is due to a strong conduction current ($R_T$ low) rather than a strong displacement current ($C_T$ high).

If $R_T = y$ and $C_T \omega = x$, then equation (3) may be written (in the event of $<$ being $=$):

$$A x^2 y^2 - y + A = 0$$

whence $$x = \pm \frac{1}{\sqrt{A}} \frac{\sqrt{y - A}}{y}$$

Figure 6:
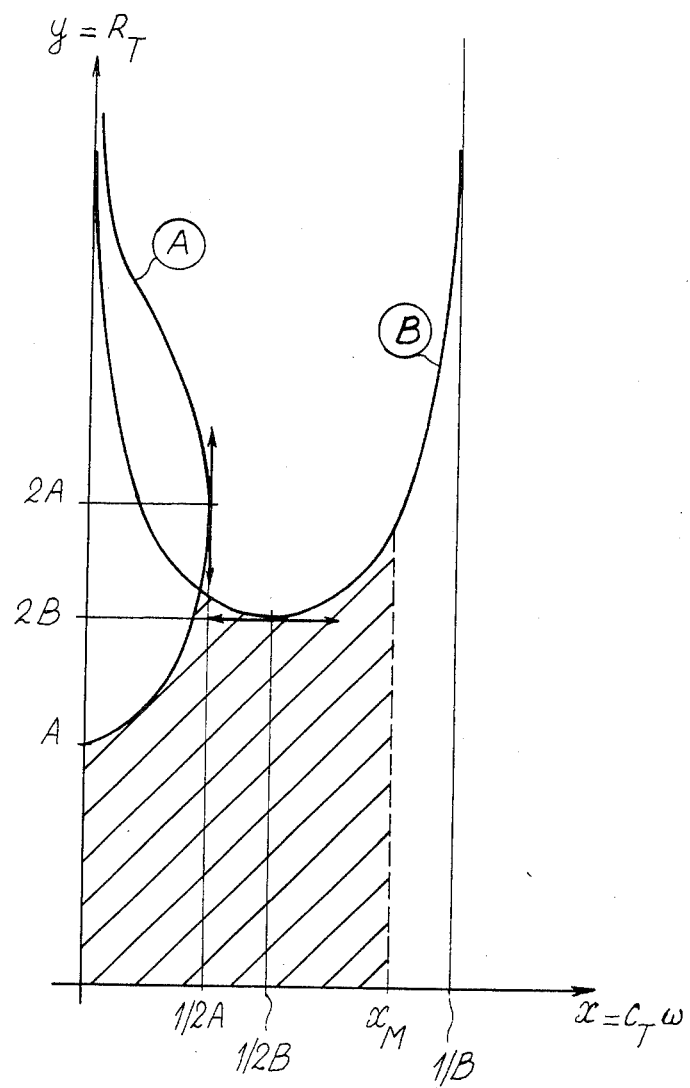
FIG. 6 shows curves explaining the block-diagram of FIG. 3.

The curve hereof is shown as (A) on FIG. 6.
Equation (4) becomes (in the event of $<$ being $=$):

$$B x^2 y^2 - xy^2 + B = 0$$

whence $$x = \frac{1}{2B} \pm \frac{\sqrt{y^2 - 4B^2}}{2By}$$

This curve is shown as (B) on FIG. 6.

In practice, the maximum dimension of the elements making up the structure and whose electrical continuity with the said structure's electrical ground is to be verified cannot give rise to values of x greater than $x_M$. By choosing $1/B > x_M$, it can be seen that conditions (3) and (4) are respected in the shaded part of the graph.

Figure 1B:
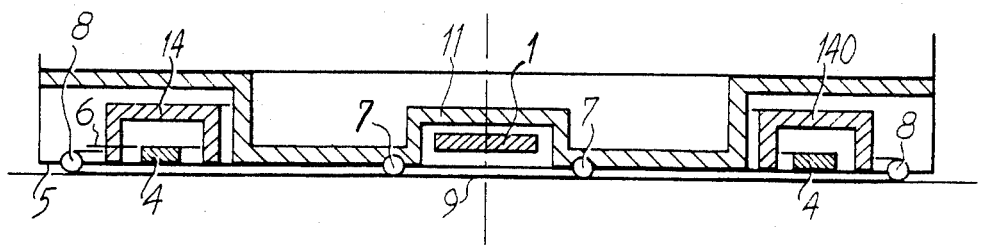
Figure 3:
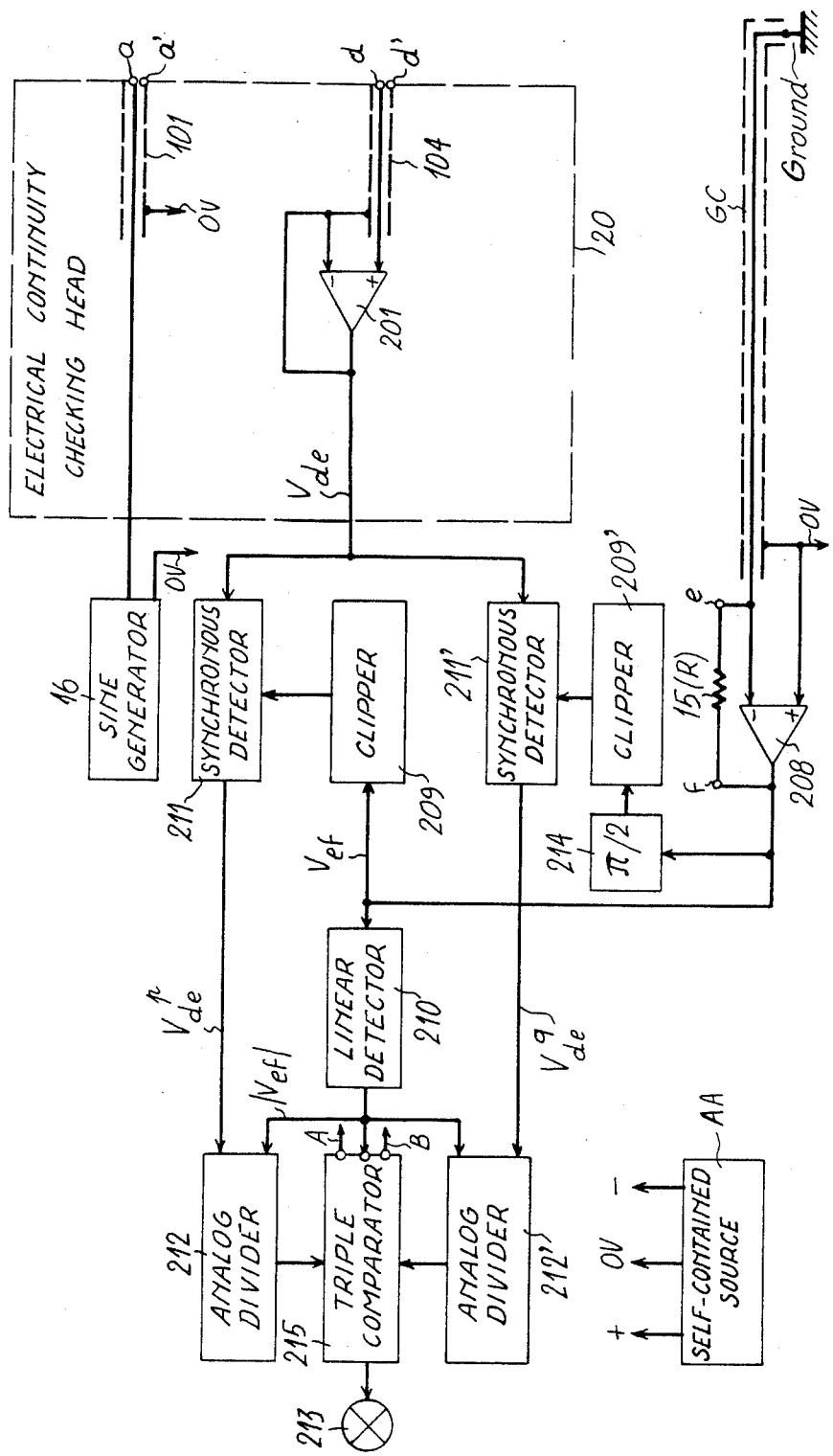
FIG. 3 depicts the electronic circuitry associated with the pick-up in FIG. 2 in block-diagram form.

The pick-up intended to come into contact with the insulating layer is shown on FIGS. 1A and 1B and is designated by the reference numeral 20. It comprises an inner cylindrical electrode 1 and an outer annular electrode 4 cylindrical and coaxial with inner electrode 1. Electrode 1 is enveloped apart from on its side resting on the insulating layer, by a sheathing electrode 11 set at a fixed potential and electrode 4 is enveloped except on its side resting on the insulating layer, by an arcing electrode 14 respectively held at the same potential as the electrode it surrounds by a unit follower which is represented on FIG. 3 as 201.

The lower surface of outer electrode 4, the edges of arcing electrode 14 and the lower plane part of sheathing electrode 11 lie in one and the same plane 5 which is slightly pocketed with respect to plane 9 along which the pick-up rest on the insulating layer. Sheathing electrode 11 envelops arcing electrode 14. The lower surface or inner electrode 1 lies in a plane 6 slightly pocketed with respect to plane 5. This electrode thus offers a lower capacitance than the other electrodes with respect to the insulating layer and, as a result, a higher impedance.

This reactive impedance is greater than the maximum resistance value of the resistive layer so that the current fed to the resistive layer is in quadrature with the supply voltage regardless of the surface resistance value in the envisioned range.

Rings 7 and 8 composed of resilient material are partially embodied in the pick-up and their lower tangent plane 9 protrudes slightly from plane 5 in such a way that they allow non-slip contact on the surface of the insulating paint layer.

Figure 2:
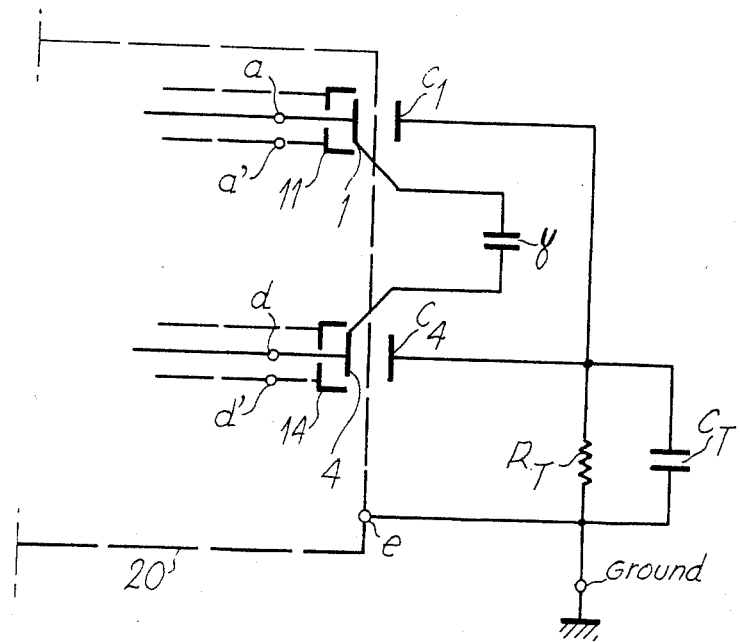
FIG. 2 is a partial electrical diagram of the pick-up of FIGS. 1A and 1B adapted for checking the electrical continuity between a structure element and the structure ground.

In reference to FIG. 2, dotted rectangle 20 represents that part of the pick-up situated at the electrode level for an electrical continuity test. The voltage $V_{ef}$ across the terminals e, f of the load resistor 15 and $V_{de}$ between terminal d of the outer electrode and ground terminal e are processed in the FIG. 3 circuit whose input terminals a, a', d, d' and e are connected to the output terminals of FIG. 2 having the same designations. Terminals a and d are connected to the inner conductor of coaxial cables 101 and 104 and terminals a' and d' connected to the outer conductors of these coaxial cables.

Sinusoïdal generator 16 is connected to terminal a and terminal zero volt of self-contained source AA. Terminal d is connected to a unit follower 201 which raises the outer conductor of coaxial cable 104 to the inner conductor voltage. Ground conductor GC is connected to amplifier 208 including load resistor 15 mounted as a feedback resistor. The output signal of unit follower 201, $V_{de}$, is applied to two synchronous detectors 211 and 211'. The voltage $V_{ef}$ across the load resistor terminals e, f is applied directly to a first clipper circuit 209 and via $\pi/2$ phase shifter 214 to a second clipper circuit 209'. The voltage across the load resistor terminals is also applied to a linear detector 210 that gives $|V_{ef}|$.

Synchronous detectors 211 and 211' receive the phase reference voltages from the clipper circuits and the voltage $V_{de}$ from amplifier 201. They deliver $V^p_{de}$ and $V^q_{de}$ respectively. Analog dividers 212 and 212' perform the divisions:

$$V^p_{de}/|V_{ef}|$$

and $$V^q_{de}/|V_{ef}|$$

which, according to formulae (1) and (2), gives the resistive and reactive components of the ground impedance.

Analog dividers 212 and 212' are connected to a triple comparator 215 which verifies conditions (3) and (4). This comparator is also connected to linear detector 210 so as to check that the voltage $|V_{ef}|$ is greater than a predetermined value.

Triple comparator 215 is connected to an indicator 213 that lights up when the three conditions checked out by the comparator have been confirmed (ground resistance smaller than A, ground capacitance smaller than B and $V_{ef}$ greater than a predetermined value).

Figure 4:
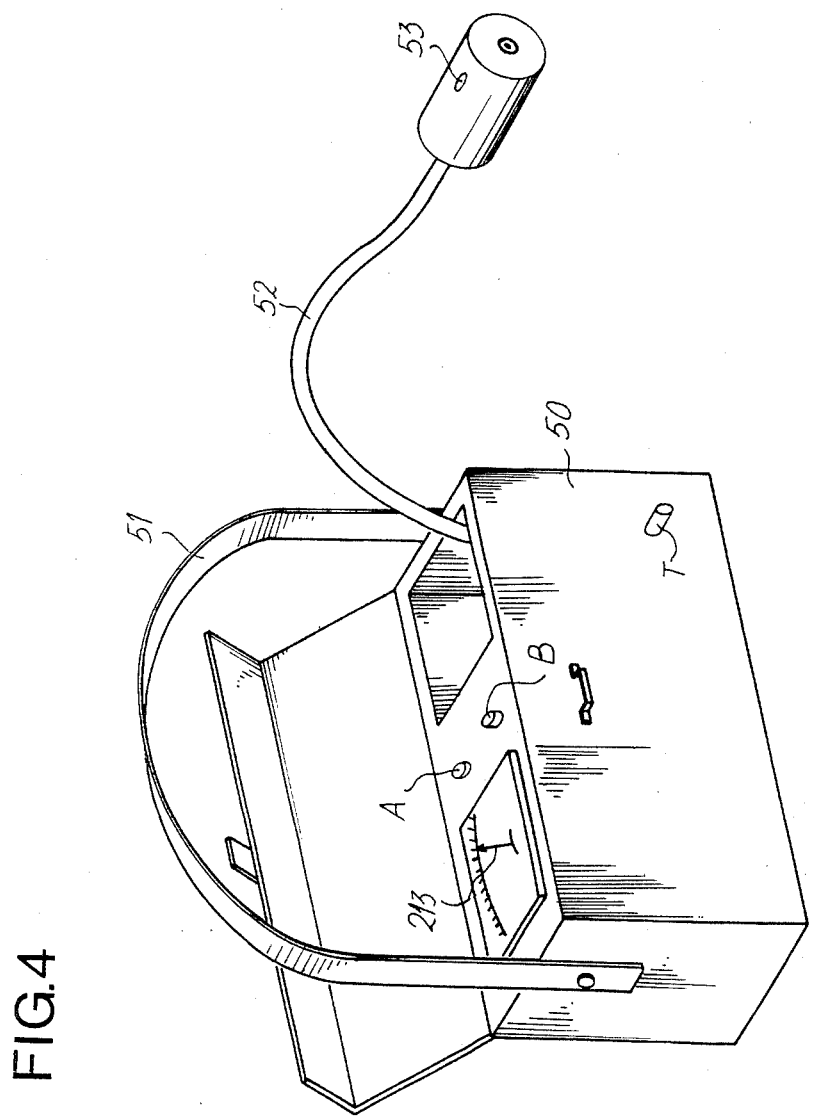
FIG. 4 depicts the invention device built and arranged as a portable equipment.

FIG. 4 depicts an embodiment of the invention in the form of portable device in two parts comprising a case 50 fitted with a strap 51 for carrying the device around the neck and, linked by a flexible cable 52, a cylindrical head including the pick-up in FIGS. 1A and 1B with electronic elements 201 and 207. A push-button 53 switches the equipment on, solely for the time required to perform an operation. The case contains all the electronic assemblies shown in FIG. 3. Indicator 213 showing the outcome of the operation is visible on the upper part of the case. Space is provided in the case for stowing the head and their connection cables when not in use.

Figure 5:
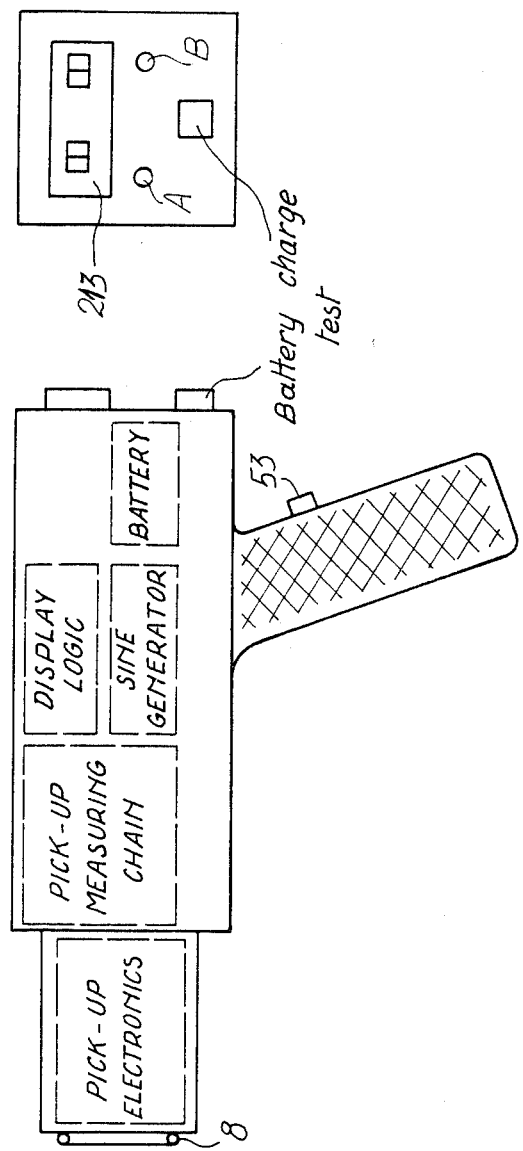
FIG. 5 depicts the invention device built and arranged in a different portable equipment form.

FIG. 5 shows another embodiment of the invention contained in a single unit. It is shaped like a pistol the barrel of which is made up of the head in FIGS. 1A-1B which may be clipped in place. Rubber ring 8 which comes into contact with the surface to be tested can be seen protruding from the head. The electronic energizing push-button 53 is placed on the pistol grip. The tell-tale indicator 213 is positioned on the rear side. In this version, 213 is no longer a needle indicator but rather a digital display.

What we claim is:

1. A continuimeter device for checking the electrical continuity of a path defined on a structure, said structure being coated with an inner resistive layer and an outer insulating superficial layer, said device comprising:
   a ground terminal electrically connected to said structure;
   a pick-up to be placed on said structure surface, formed of an inner cylindrical electrode and an outer annular electrode coaxial with said inner electrode;
   means for applying a supply alternating voltage between said inner electrode and said ground terminal, thereby producing a current between said inner electrode and ground terminal;
   means for applying said current to a load resistor and measuring the voltage across said load resistor;
   means for measuring the voltage appearing between said outer electrode and ground terminal;
   means for forming two components of said voltage between said outer electrode and ground terminal, respectively cophasal and in phase quadrature with said load resistor voltage;
   means for dividing each of said component voltages by said load resistor voltage, thereby providing two divided voltages; and
   means for comparing said two divided voltages to respectively two predetermined voltages.

2. A continuimeter device for checking the electrical continuity of a path defined on a structure, said structure being coated with an inner resistive layer and an outer insulating superficial layer, said device comprising:
   a ground terminal electrically connected to said structure;
   a pick-up to be placed on said structure surface, formed of an inner cylindrical electrode and an outer annular electrode coaxial with said inner electrode;
   an annular arcing electrode surrounding said outer electrode except on the part thereof lying on the structure surface;
   unit follower means bringing said arcing electrode to a potential equal to that of the surrounded outer electrode;
   means for applying a supply alternating voltage between said inner electrode and said ground terminal, thereby producing a current between said inner electrode and ground terminal;
   means for applying said current to a load resistor and measuring the voltage across said load resistor;
   means for measuring the voltage appearing between said outer electrode and ground terminal;
   means for forming two components of said voltage between said outer electrode and ground terminal, respectively cophasal and in phase quadrature with said load resistor voltage;
   means for dividing each of said component voltages by said load resistor voltage, thereby providing two divided voltages; and
   means for comparing said two divided voltages to respectively two predetermined voltages.

3. A continuimeter device for checking the electrical continuity of a path defined on a structure, said structure being coated with an inner resistive layer and an outer insulating superficial layer, said device comprising:
   a ground terminal electrically connected to said structure;
   a pick-up to be placed on said structure surface, formed of an inner cylindrical electrode and an outer annular electrode coaxial with said inner electrode;
   an annular arcing electrode surrounding said outer electrode except on the part thereof lying on the structure surface;
   unit follower means bringing said arcing electrode to a potential equal to that of the surrounded outer electrode;
   a sheathing electrode surrounding said inner electrode except on the part therof lying on the structure surface, said sheathing electrodes being brought to a predetermined potential;
   means for applying a supply alternating voltage between said inner electrode and said ground terminal, thereby producing a current between said inner electrode and ground terminal;
   means for applying said current to a load resistor and measuring the voltage across said load resistor;
   means for measuring the voltage appearing between said outer electrode and ground terminal;
   means for forming two components of said voltage between said outer electrode and ground terminal, respectively cophasal and in phase quadrature with said load resistor voltage;
   means for dividing each of said component voltages by said load resistor voltage, thereby providing two divided voltages; and
   means for comparing said two divided voltages to respectively two predetermined voltages.

4. A continuimeter device for checking the electrical continuity of a path defined on a structure, said structure being coated with an inner resistive layer and an outer insulating superficial layer, said device comprising:
   a ground terminal electrically connected to said structure;
   a pick-up to be placed on said structure surface, formed of an inner cylindrical electrode, and an outer annular electrode coaxial with said inner electrode, said outer electrode having its end located in a first plane and said inner electrode having its end located in a second plane more distant from the structure surface than said first plane, whereby said inner electrode has with respect to the structure surface an impedance larger than the impedance of the outer electrode with respect to said surface;

means for applying a supply alternating voltage between said inner electrode and said ground terminal, thereby producing a current between said inner electrode and ground terminal;

means for applying said current to a load resistor and measuring the voltage across said load resistor;

means for measuring the voltage appearing between said outer electrode and ground terminal;

means for forming two components of said voltage between said outer electrode and ground terminal, respectively cophasal and in phase quadrature with said load resistor voltage;

means for dividing each of said component voltages by said load resistor voltage, thereby providing two divided voltages; and means for comparing said two divided voltages to respectively two predetermined voltages.

* * * * *